(12) United States Patent
Maksimainen et al.

(10) Patent No.: US 11,258,386 B2
(45) Date of Patent: Feb. 22, 2022

(54) WIND TURBINE ASSEMBLY

(71) Applicant: ABB Schweiz AG, Baden (CH)

(72) Inventors: Petri Maksimainen, Helsinki (FI); Teemu Oksanen, Helsinki (FI); Erkki Niemi, Helsinki (FI); Tuomas Stark, Helsinki (FI)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 17/163,655

(22) Filed: Feb. 1, 2021

(65) Prior Publication Data
US 2021/0265931 A1    Aug. 26, 2021

(30) Foreign Application Priority Data

Feb. 20, 2020   (EP) .................................... 20158426

(51) Int. Cl.
| | |
|---|---|
| *H02P 9/00* | (2006.01) |
| *F03D 9/22* | (2016.01) |
| *F03D 9/25* | (2016.01) |
| *F03D 80/60* | (2016.01) |
| *F03D 7/02* | (2006.01) |
| *G01K 3/00* | (2006.01) |

(Continued)

(52) U.S. Cl.
CPC ............ *H02P 9/006* (2013.01); *F03D 7/0224* (2013.01); *F03D 7/0244* (2013.01); *F03D 9/22* (2016.05); *F03D 9/25* (2016.05); *F03D 80/60* (2016.05); *G01K 3/005* (2013.01); *G01N 33/0063* (2013.01); *H02J 3/1842* (2013.01); *H03H 7/0115* (2013.01); *H01L 2924/1425* (2013.01); *H02P 2101/15* (2015.01)

(58) Field of Classification Search
CPC ........ H02J 3/1842; F03D 9/22; F03D 7/0224; F03D 80/60; G01K 3/005; H01L 2924/1425; H02P 2101/15

USPC ...................................................... 290/44, 55
See application file for complete search history.

(56) References Cited

U.S. PATENT DOCUMENTS

| | | | |
|---|---|---|---|
| 8,994,206 B2 * | 3/2015 | Bala ........................ | H02J 3/381 |
| | | | 290/55 |
| 9,722,502 B2 * | 8/2017 | Steimer ................. | H02M 5/293 |

(Continued)

FOREIGN PATENT DOCUMENTS

| | | |
|---|---|---|
| CN | 110752737 A | 2/2020 |
| DE | 102007054215 A1 | 5/2009 |
| GB | 2190231 A | 11/1987 |

OTHER PUBLICATIONS

Extended European Search Report; Application No. 20158426.5; dated Aug. 20, 2020; dated Aug. 28, 2020; 7 Pages.

*Primary Examiner* — Charles Reid, Jr.
(74) *Attorney, Agent, or Firm* — Whitmyer IP Group LLC

(57) ABSTRACT

A wind turbine assembly including a rotor system, a generator, a first converter, a second converter, and a controller system. The first converter includes a first bridge circuit having a plurality of switch members each having a controllable switch. The second converter includes a second bridge circuit having a plurality of switch members each having a controllable switch. The controller system is adapted to provide a drying operation for second converter including short circuiting the second converter with the controllable switches of the second bridge in circuit, and supplying power from the generator through the first converter to the short circuited second converter for drying the second converter.

16 Claims, 1 Drawing Sheet

(51) Int. Cl.
    *G01N 33/00*     (2006.01)
    *H02J 3/18*     (2006.01)
    *H03H 7/01*     (2006.01)
    *H02P 101/15*     (2016.01)

(56) References Cited

U.S. PATENT DOCUMENTS

| | | | |
|---|---|---|---|
| 10,374,431 B2* | 8/2019 | Canales | H02J 3/46 |
| 2006/0137214 A1* | 6/2006 | Achenbach | H05K 5/0213 |
| | | | 34/468 |
| 2010/0253079 A1* | 10/2010 | Bolin | F03D 80/60 |
| | | | 290/44 |
| 2012/0025535 A1* | 2/2012 | Sihler | H02J 3/386 |
| | | | 290/55 |
| 2013/0207394 A1* | 8/2013 | Banham-Hall | H02P 9/48 |
| | | | 290/44 |
| 2014/0339830 A1* | 11/2014 | Gupta | F03D 9/255 |
| | | | 290/44 |
| 2015/0249414 A1* | 9/2015 | Barker | H02J 3/386 |
| | | | 290/44 |
| 2018/0340519 A1* | 11/2018 | Schult | F03D 7/0284 |
| 2020/0392942 A1* | 12/2020 | Andersen | F03D 7/0272 |

* cited by examiner

WIND TURBINE ASSEMBLY

TECHNICAL FIELD

The present invention relates to a wind turbine assembly, and more particularly to drying of electrical components of a wind turbine assembly.

BACKGROUND

During commissioning of a wind turbine assembly, there might be excessive moisture in electrical components of the wind turbine assembly. The excessive moisture can cause breakthroughs in the electrical components, thereby causing damages in the electrical components. Consequently, it is important to remove excessive moisture from electrical components of a wind turbine assembly before starting up the wind turbine assembly.

A known wind turbine assembly comprises a heating resistor system for removing excessive moisture from electrical components of the wind turbine assembly. The heating resistor system comprises heating resistors for heating electric converters of the wind turbine assembly, the heating resistors being located outside the electric converters.

One of the disadvantages associated with the above known wind turbine assembly is that the heating resistor system requires space in the assembly, and incurs extra costs.

SUMMARY

An object of the present invention is to provide a wind turbine assembly so as to alleviate the above disadvantages. The objects of the invention are achieved by a wind turbine assembly, which is characterized by what is stated in the independent claim. The preferred embodiments of the invention are disclosed in the dependent claims.

The invention is based on the idea of drying a grid side converter of a wind turbine assembly by short circuiting the grid side converter with controllable switches thereof, and supplying power from a generator of the wind turbine assembly through a generator side converter of the wind turbine assembly to the short circuited grid side converter for drying the grid side converter, wherein during the drying operation, voltage of the generator is kept so low that no breakthroughs occur, and currents in electrical components of the wind turbine assembly remain sufficiently low.

In an embodiment of the invention, a generator side converter is short-circuited first, and after the generator side converter is sufficiently dry, a grid side converter is short-circuited, and power is supplied to the short-circuited grid side converter by the previously dried generator side converter.

An advantage of a wind turbine assembly of the invention is its compact size and low costs due to possibility to omit a heating resistor system from the wind turbine assembly.

BRIEF DESCRIPTION OF THE DRAWINGS

In the following the invention will be described in greater detail by means of preferred embodiments with reference to the attached drawings, in which.

DETAILED DESCRIPTION

Figure 1:
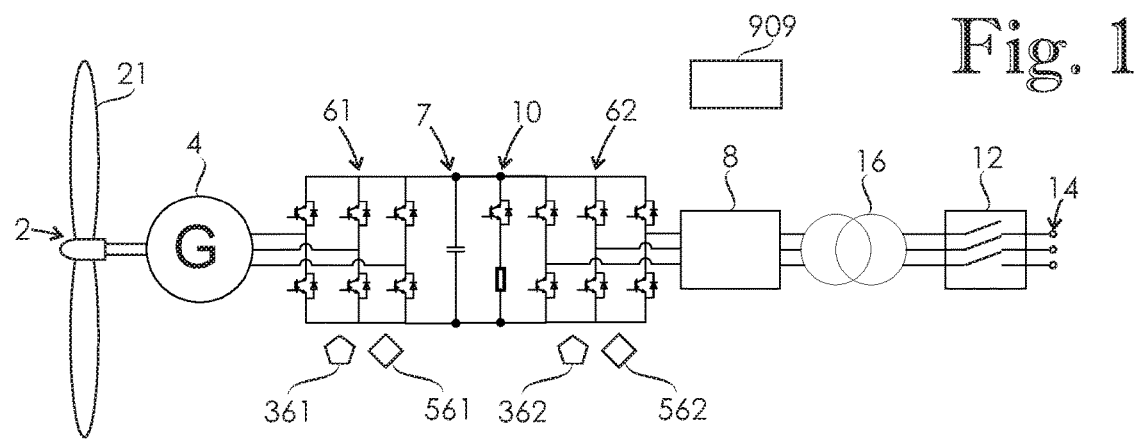
FIG. 1 shows a wind turbine assembly according to an embodiment of the invention.

FIG. 1 shows a wind turbine assembly comprising a rotor system 2, a generator 4, a first converter 61, a DC link 7, a second converter 62, an LC filter 8, a brake chopper 10, a circuit breaker 12, a transformer 16, an alternating current output 14, a sensor system, and a controller system 909.

The rotor system 2 is adapted to convert kinetic energy of wind into rotational energy of the rotor system 2. The rotor system 2 comprises a plurality of adjustable blades 21.

The generator 4 is adapted to be rotated by the rotor system 2 for converting the rotational energy of the rotor system 2 into electrical energy. The generator 4 is a permanent magnet generator, and is adapted to generate an alternating current. A voltage of the generator 4 is adapted to be controlled by adjusting blade angles of the plurality of adjustable blades 21. In an alternative embodiment, the generator is a separately excited synchronous generator, and the voltage of the generator is adapted to be controlled by adjusting exciting current of the generator.

The first converter 61 has an alternating current side connected electrically to the generator 4, and a direct current side connected electrically to the DC link 7 that comprises DC link capacitance. The second converter 62 has a direct current side connected electrically to the direct current side of the first converter 61 through the DC link 7, and an alternating current side connected electrically to the alternating current output 14 of the wind turbine assembly through the LC filter 8, the transformer 16 and the circuit breaker 12.

Herein, two components are defined to be connected electrically to each other when there is a connection between the components enabling transfer of electric energy between the components.

Figure 2:
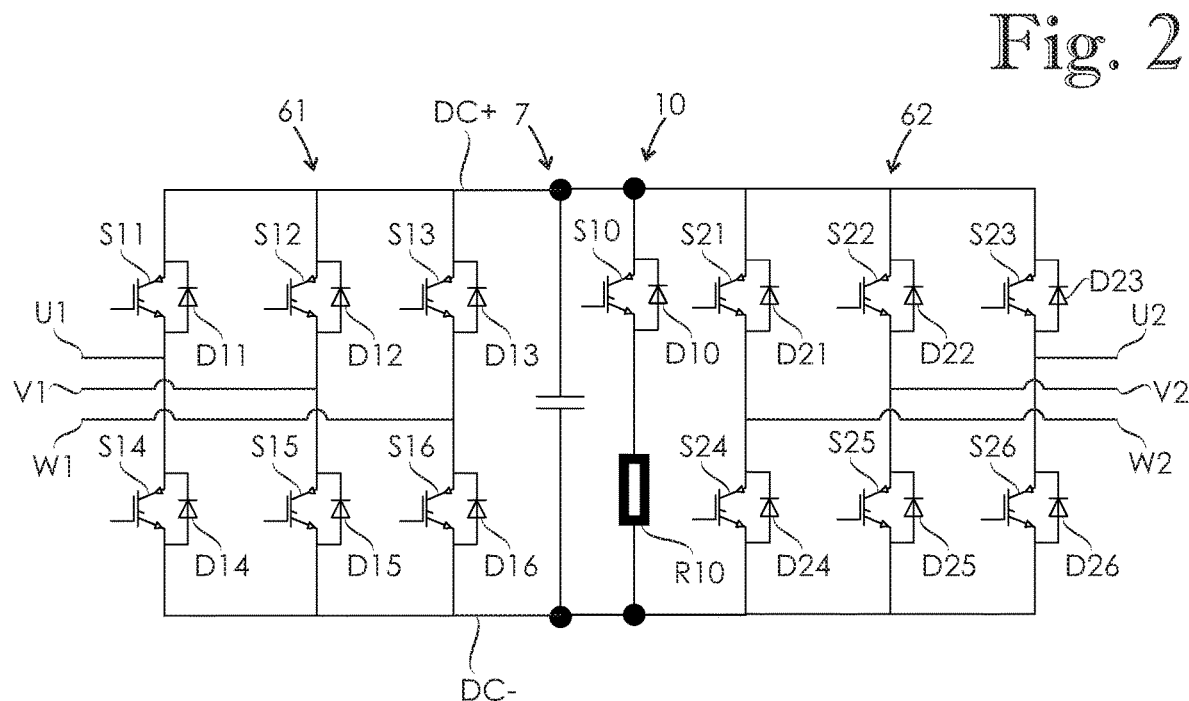
FIG. 2 shows an enlargement of a portion of the wind turbine assembly of FIG. 1.

Referring now to FIG. 2, the alternating current side of the first converter 61 is connected electrically to phases U1, V1 and W1, and the alternating current side of the second converter 62 is connected electrically to phases U2, V2 and W2. The DC link 7 comprises a positive busbar DC+ and a negative busbar DC−, to which the direct current sides of the first converter 61 and second converter 62 are connected electrically.

The first converter 61 comprises a first bridge circuit having six switch members, and the second converter 62 comprises a second bridge circuit having six switch members. Each of the switch members has a controllable switch and a diode connected antiparallel with the controllable switch. The controllable switches of the first bridge circuit are denoted with reference signs S11 to S16, and corresponding diodes are denoted with reference signs D11 to D16. The controllable switches of the second bridge circuit are denoted with reference signs S21 to S26, and corresponding diodes are denoted with reference signs D21 to D26.

The controllable switches S11 to S16 of the first bridge circuit and the controllable switches S21 to S26 of the second bridge circuit are insulated-gate bipolar transistors, or IGBTs. In alternative embodiments, the controllable switches comprise other types of semiconductor switches such as field-effect transistors, or FETs.

The first converter 61 and second converter 62 are bidirectional converters. The first converter 61 and second converter 62 are functionally identical electric power converters.

The brake chopper 10 is connected electrically between the positive busbar DC+ of the DC link 7 and the negative busbar DC− of the DC link 7. The brake chopper 10 comprises a brake chopper switch member and a brake resistor R10 connected in series. The brake chopper switch member comprises a controllable brake chopper switch S10 and a diode D10 connected antiparallel with the controllable brake chopper switch S10.

The LC filter 8 is connected electrically between the alternating current side of the second converter 62 and the transformer 16. The LC filter 8 comprises an inductor and a capacitor. LC filters are known in the art. Herein, expression "LC filter" covers also LCL filters.

The controller system 909 is adapted to control the first converter 61 and second converter 62, the brake chopper switch S10, and blade angles of the plurality of adjustable blades 21. The controller system 909 is adapted to provide a drying operation for first converter 61, a drying operation for the brake chopper 10, a drying operation for second converter 62, and a drying operation for additional electric system 8, 16.

The drying operation for first converter comprises short circuiting the first converter 61 with the controllable switches of the first bridge circuit, and supplying power from the generator 4 to the short circuited first converter 61 for drying the first converter 61. In the drying operation for first converter, the first converter 61 is short circuited by short circuiting the phases U1, V1 and W1 with the controllable switches of the first bridge circuit. During the drying operation for first converter, voltage of the generator 4 is kept lower than the nominal output voltage of the generator 4 by adjusting blade angles of the plurality of adjustable blades 21 with the controller system 909.

In an embodiment, the drying operation for first converter comprises short circuiting the first converter 61 by controlling the controllable switches S11, S12 and S13 of the first bridge circuit to conducting state. In another embodiment, the drying operation for first converter comprises short circuiting the first converter 61 by controlling the controllable switches S14, S15 and S16 of the first bridge circuit to conducting state. In yet another embodiment, the drying operation for first converter comprises short circuiting the first converter 61 by controlling all of the controllable switches S11 to S16 of the first bridge circuit to conducting state.

The drying operation for the brake chopper is carried out subsequent to the drying operation for first converter. In an embodiment, the drying operation for the brake chopper is carried out subsequent to the drying operation for second converter. In an alternative embodiment, the drying operation for the brake chopper is carried out concurrently with the drying operation for second converter.

The drying operation for the brake chopper comprises controlling the brake chopper switch S10 to conducting state, and supplying power from the generator 4 through the first converter 61 to the brake resistor R10. In an embodiment, the drying operation for the brake chopper comprises controlling all of the controllable switches S11 to S16 of the first bridge circuit to non-conducting state, wherein power is supplied through the first converter 61 via diodes D11-D16.

The drying operation for second converter is carried out subsequent to the drying operation for first converter. The drying operation for second converter comprises short circuiting the second converter 62 with the controllable switches of the second bridge circuit, and supplying power from the generator 4 through the first converter 61 to the short circuited second converter 62 for drying the second converter 62.

The drying operation for second converter comprises short circuiting the second converter 62 by providing a short circuit between the positive busbar DC+ and negative busbar DC− with the controllable switches of the second converter 62. In an embodiment, the drying operation for second converter comprises short circuiting the second converter 62 by controlling all of the controllable switches S21 to S26 of the second bridge circuit to conducting state. In another embodiment, the drying operation for second converter comprises short circuiting the second converter 62 by controlling the controllable switches S21 and S24 of the second bridge circuit to conducting state. In yet another embodiment, the drying operation for second converter comprises short circuiting the second converter 62 by controlling the controllable switches S22 and S25 of the second bridge circuit to conducting state. In yet another embodiment, the drying operation for second converter comprises short circuiting the second converter 62 by controlling the controllable switches S23 and S26 of the second bridge circuit to conducting state.

During the drying operation for second converter, power is supplied through the first converter 61 for example by controlling the controllable switches of the first bridge circuit to non-conducting state by the controller system 909, wherein power is supplied from the first converter 61 to the short circuited second converter 62 through the diodes D11-D16 of the first bridge circuit.

During the drying operation for second converter, voltage of the generator 4 is kept lower than the nominal output voltage of the generator 4 by adjusting blade angles of the plurality of adjustable blades 21 with the controller system 909. Further, during the drying operation for second converter, the controller system 909 is adapted to control voltage of the generator 4 such that currents of the generator 4, first converter 61 and second converter 62 are lower than or equal to corresponding nominal currents. In an alternative embodiment, during the drying operation for second converter, voltage of the generator is controlled such that currents of the generator, first converter and second converter are lower than or equal to 120% of corresponding nominal currents. It is possible to slightly exceed nominal currents since the drying operation for second converter is a temporary operation with relatively short duration.

Since DC link 7 is located between the first converter 61 and second converter 62, the drying operation for second converter inherently also dries the DC link 7. In an embodiment, duration of the drying operation for second converter is determined based on humidity information from both the second converter and the DC link.

The alternating current output 14 of the wind turbine assembly is adapted to be connected to an electrical network. The circuit breaker 12 is located electrically between the transformer 16 and the alternating current output 14 of the wind turbine assembly. Therefore, the circuit breaker 12 is adapted to disconnect the alternating current side of the second converter 62 from the alternating current output 14 of the wind turbine assembly.

During the drying operation for first converter, the drying operation for the brake chopper, the drying operation for second converter and the drying operation for additional electric system, the circuit breaker 12 is in non-conducting state. Consequently, the drying operation for first converter, the drying operation for the brake chopper, the drying operation for second converter, and the drying operation for additional electric system are carried out by energy supplied by the generator 4.

The sensor system comprises a humidity sensor 361 for measuring humidity relating to the first converter 61, a temperature sensor 561 for measuring temperature relating to the first converter 61, a humidity sensor 362 for measuring humidity relating to the second converter 62, and a temperature sensor 562 for measuring temperature relating to the second converter 62.

The sensor system is communicatively connected to the controller system 909. The controller system 909 is adapted to terminate the drying operation for first converter when information received from the sensor system indicates that a humidity level of the first converter 61 has dropped to an acceptable level. Further, the controller system 909 is adapted to terminate the drying operation for second converter when information received from the sensor system indicates that a humidity level of the second converter 62 has dropped to an acceptable level. When humidity levels of the first converter 61 and second converter 62 are on acceptable levels, the first converter 61 and second converter 62 can be operated normally.

In an alternative embodiment, the controller system 909 is adapted to terminate the drying operation for second converter when a humidity level of the second converter has dropped to an acceptable level, and to terminate the drying operation for additional electric system when a humidity level of the additional electric system has dropped to an acceptable level. In another alternative embodiment, each drying operation has a predetermined duration, wherein the humidity levels are assumed to be on acceptable levels after the predetermined durations.

The drying operation for additional electric system is carried out subsequent to the drying operation for second converter. The drying operation for additional electric system comprises providing a drying current in at least one additional electric system for drying the at least one additional electric system, the drying current being lower than or equal to corresponding nominal current. Power for the drying current in the at least one additional electric system is supplied from the generator through the first converter and second converter.

The drying operation for additional electric system comprises controlling all of the controllable switches S11 to S16 of the first bridge circuit to non-conducting state, wherein power is supplied through the first converter 61 via diodes D11-D16, and controlling the controllable switches S21 to S26 of the second bridge circuit such that suitable heating current flows through the capacitor of the LC filter 8.

In an alternative embodiment, the drying operation for additional electric system comprises controlling all of the controllable switches S11 to S16 of the first bridge circuit to non-conducting state, and controlling switches S22 and S24 of the second bridge circuit to conducting state, wherein power is supplied through the first converter 61 and switches S22 and S24 to the transformer, and heat is generated in the transformer 16 for drying the transformer 16.

It will be obvious to a person skilled in the art that the inventive concept can be implemented in various ways. The invention and its embodiments are not limited to the examples described above but may vary within the scope of the claims.

The invention claimed is:

1. A wind turbine assembly comprising:
   a rotor system;
   a generator for generating an alternating current, the generator having a nominal output voltage, and being adapted to be rotated by the rotor system;
   a first converter having an alternating current side connected electrically to the generator, and a direct current side, the first converter comprising a first bridge circuit having a plurality of switch members each having a controllable switch and a diode connected antiparallel with the controllable switch;
   a second converter having a direct current side connected electrically to the direct current side of the first converter, and an alternating current side, the second converter comprising a second bridge circuit having a plurality of switch members each having a controllable switch; and
   a controller system adapted to control the first converter and second converter,
   wherein the controller system is adapted to provide a drying operation for the second converter comprising:
   short circuiting the second converter with the controllable switches of the second bridge circuit; and
   supplying power from the generator through the first converter to the short circuited second converter for drying the second converter.

2. The wind turbine assembly according to claim 1, wherein during the drying operation for the second converter, voltage of the generator is lower than the nominal output voltage of the generator.

3. The wind turbine assembly according to claim 1, wherein the drying operation for the second converter includes controlling the controllable switches of the first bridge circuit to a non-conducting state, wherein power is supplied from the first converter to the short circuited second converter through the plurality of diodes of the first bridge circuit.

4. The wind turbine assembly as claimed in claim 1, wherein during the drying operation for the second converter, voltage of the generator is controlled such that currents of the generator, first converter and second converter are lower than or equal to corresponding nominal currents.

5. The wind turbine assembly as claimed in claim 1, wherein the wind turbine assembly further comprises:
   an alternating current output adapted to be connected to an electrical network; and
   a circuit breaker located electrically between the alternating current side of the second converter and the alternating current output of the wind turbine assembly,
   wherein during the drying operation for the second converter, the circuit breaker is in a non-conducting state.

6. The wind turbine assembly as claimed in claim 1, wherein the wind turbine assembly further comprises a sensor system communicatively connected to the controller system, wherein the sensor system includes at least one humidity sensor for measuring humidity relating to the second converter, and the controller system is adapted to terminate the drying operation for the second converter when information received from the sensor system indicates that a humidity level of the second converter has dropped to an acceptable level.

7. The wind turbine assembly as claimed in claim 1, wherein the controller system is adapted to provide a drying operation for the first converter including:
   short circuiting the first converter with the controllable switches of the first bridge circuit; and
   supplying power from the generator to the short circuited first converter for drying the first converter,
   wherein the drying operation for the first converter is carried out prior to the drying operation for the second converter.

8. The wind turbine assembly according to claim 7, wherein during the drying operation for the first converter, voltage of the generator is lower than the nominal output voltage of the generator.

9. The wind turbine assembly as claimed in claim 1, wherein the wind turbine assembly includes at least one additional electric system connected electrically to the alternating current side of the second converter, and the controller system is adapted to provide a drying operation for the at least one additional electric system comprising providing a drying current in the at least one additional electric system for drying the at least one additional electric system, the drying current being lower than or equal to corresponding nominal current, wherein the drying operation for the at least one additional electric system is carried out subsequent to the drying operation for the second converter, and power for the drying current in the at least one additional electric system is supplied from the generator through the first converter and second converter.

10. The wind turbine assembly according to claim 9, wherein the least one additional electric system includes an LC filter and/or a transformer.

11. The wind turbine assembly as claimed in claim 1, wherein the wind turbine assembly further comprises:
  a DC link comprising a positive busbar and a negative busbar, to which the direct current sides of the first converter and second converter are connected electrically; and
  a brake chopper connected electrically between the positive busbar of the DC link and the negative busbar of the DC link, the brake chopper comprising a brake chopper switch member and a brake resistor connected in series, wherein the brake chopper switch member includes a controllable brake chopper switch adapted to be controlled by the controller system, and
  wherein the controller system is adapted to provide a drying operation for the brake chopper comprising controlling the brake chopper switch to a conducting state, and supplying power from the generator through the first converter to the brake resistor for drying the brake chopper.

12. The wind turbine assembly according to claim 11, wherein the controller system is adapted to carry out the drying operation for the brake chopper subsequent to the drying operation for the second converter, or concurrently with the drying operation for the second converter.

13. The wind turbine assembly as claimed in claim 1, wherein the rotor system includes at least one adjustable blade, the controller system is adapted to control blade angle of the at least one adjustable blade, and the generator is a permanent magnet generator, wherein the drying operation for the second converter includes adjusting blade angle of the at least one adjustable blade in order to provide a suitable generator voltage.

14. The wind turbine assembly as claimed in claim 1, wherein during the drying operation for the second converter, voltage of the generator is controlled such that currents of the generator, first converter and second converter are lower than or equal to 120% of corresponding nominal currents.

15. The wind turbine assembly as claimed in claim 1, wherein the wind turbine assembly includes a sensor system communicatively connected to the controller system, wherein the sensor system includes at least one humidity sensor for measuring humidity relating to the second converter, and at least one temperature sensor for measuring temperature relating to the second converter, and the controller system is adapted to terminate the drying operation for the second converter when information received from the sensor system indicates that a humidity level of the second converter has dropped to an acceptable level.

16. The wind turbine assembly as claimed in claim 1, wherein the wind turbine assembly includes a sensor system communicatively connected to the controller system, wherein the sensor system includes at least one temperature sensor for measuring temperature relating to the second converter, and the controller system is adapted to terminate the drying operation for the second converter when information received from the sensor system indicates that a humidity level of the second converter has dropped to an acceptable level.

\* \* \* \* \*